United States Patent [19]

Cook

[11] Patent Number: 4,534,912
[45] Date of Patent: Aug. 13, 1985

[54] PREPARATION OF ANHYDRIDES
[75] Inventor: John Cook, Sproatley, England
[73] Assignee: BP Chemicals Limited, London, England
[21] Appl. No.: 611,348
[22] Filed: May 17, 1984
[30] Foreign Application Priority Data May 21, 1983 [GB] United Kingdom ............... 8314137

[51] Int. Cl.$^3$ ............................................. C07C 51/56
[52] U.S. Cl. ..................................................... 260/549
[58] Field of Search ................... 260/549, 546, 544 A
[56] References Cited
U.S. PATENT DOCUMENTS 2,730,546 1/1956 Reppe et al. .................... 260/549

Primary Examiner—Natalie Trousof
Assistant Examiner—L. Hendriksen
Attorney, Agent, or Firm—Brooks, Haidt, Haffner & Delahunty

[57] ABSTRACT

Acetic anhydride is prepared by reacting, at elevated temperature, methyl acetate or dimethyl ether with carbon monoxide in the presence of an effective amount of a catalyst which comprises: (1) cobalt, (2) a compound containing at least one quaternary nitrogen or phosphorus atom and (3) a source of iodide or bromide wherein the atomic ratio of iodide or bromide to cobalt is from 0.5:1 to 5:1. The compound containing at least one quaternary nitrogen or phosphorus atom can optionally be generated in situ by a quaternization reaction.

10 Claims, No Drawings

PREPARATION OF ANHYDRIDES

This invention relates to a process for the preparation of acetic anhydride by reaction of methyl acetate or dimethyl ether with carbon monoxide.

European patent application No. 025702 discloses a process which comprises reacting methyl acetate or dimethyl ether with hydrogen and carbon monoxide in the presence of a cobalt catalyst, an amine or phosphine and iodide. Although the object of the process is to produce ethylidene diacetate, acetic anhydride is produced as a coproduct in some of the worked examples. Further the catalyst systems described contain high halide concentrations which have the disadvantage that they can be corrosive.

It has now been found that the reaction to form acetic anhydride can be significantly improved by modifying the catalyst system to one of low halide concentration.

Thus, according to the present invention a process for the preparation of acetic anhydride comprises reacting at elevated temperature methyl acetate or dimethyl ether with carbon monoxide characterised in that the reaction is carried out in the presence of an effective amount of a catalyst comprising:

(1) cobalt,
(2) a compound containing at least one quaternary nitrogen or phosphorus atom,
(3) a source of iodide or bromide wherein the atomic ratio of iodide or bromide to cobalt is from 0.5:1 to 5:1.

Preferably the atomic ratio of iodide or bromide to cobalt is from 0.5:1 to 2:1.

The cobalt may be added in any convenient form, e.g. in the zero valent state or in any higher valent form. Thus, the cobalt may be added as the elemental metal in finely divided form, or as the carbonyl, or as the carbonate, oxide, hydroxide, bromide, iodide, chloride, lower alkoxide such as methoxide, phenoxide, or carboxylate wherein the carboxylate anion is derived from an alkanoic acid of 1 to 20 carbon atoms. Similarly, complexes of the metal can be employed, for example, the cobalt may be coordinated with one or more ligands selected from carbon monoxide, halides, phosphines, arsines and trivalent nitrogen compounds. Suitably, cobalt may be added as a halide, a carboxylate salt, a carbonyl or a carbonyl halide.

The compound containing at least one quaternary nitrogen or phosphorus atom can be a salt of any convenient anion for example halide, carboxylate, tosylate and the like. The quaternary nitrogen or phosphorus atom may be supplied as more than one salt, as for example where it is desirable to add small amounts of iodide or bromide while adding larger amounts of the quaternary nitrogen or phosphorus.

The quaternary nitrogen or phosphorus compound can also be added to the reactor as two precursors, the first being a trivalent nitrogen or phosphorus compound capable of forming the quaternary compound under the reaction conditions, the second being conveniently a halide-free quaternizing agent.

The trivalent nitrogen compound can be any such compound which is able to undergo quaternisation. Suitable trivalent nitrogen compounds include heterocyclic amines such as pyridine, picoline, quinoline, hydroxyquinoline, methylquinoline, pyrrole, pyrrolidine, pyrrolidone and the like or an imidazole, such as imidazole, N-methylimidazole and the like. Suitable trivalent phosphorus compounds are of formula:

wherein $R^1$, $R^2$ and $R^3$ which may be the same or different are alkyl groups of up to 20, preferably from 1 to 8, carbon atoms or monocyclic aryl groups, or $R^3$ may be the group:

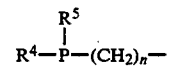

wherein $R^4$ and $R^5$ are each a monocyclic aryl group or an alkyl group and n is zero or an integer in the range 1 to 20. Suitable compounds having the above formula include trimethylphosphine, tripropylphosphine and triphenylphosphine.

The quaternizing agent is conveniently a halide free-alkylating agent preferably a methylation agent. Suitable methylating agents are of formula

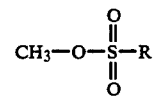

where R is hydrogen, an alkyl or aryl group or an alkoxy or aryloxy group, or F or $CF_3$. Examples are methyl p-toluenesulphonate, dimethyl sulphate, methyl sulphonic acid, and methyl fluorosulphonic acid.

By halide-free is meant not containing chlorine, bromine or iodine.

Preferably the ratio of moles of alkylating agent to gm atoms of cobalt is at least 5:1 more preferably at least 20:1 and can exceed 50:1.

Although the molar ratio of the first precursor to the second precursor may vary over a wide range, it may suitably be in the range from 0.1:1 to 5:1. It has been found that the catalyst efficiency increases as the ratio approaches 1:1 from either direction. Accordingly, a molar ratio of about 1:1 e.g. from 0.5:1 to 1.5:1 is preferred.

Suitable quaternary nitrogen- or phosphorus-containing compounds which may be added directly or generated by the method described above are thus, for example, the salts of the organic cations N-methylpyridinium, N,N-dimethylimidazolium, N-methylquinolinium, tetramethyl phosphonium, ethyltrimethyl phosphonium, methyltripropyl phosphonium and methyltriphenyl phosphonium.

The source of iodide or bromide can be any convenient source both organic or inorganic including alkali metal iodides or bromides, iodine and the like.

A copromoter in the form of a lower monocarboxylic acid may be employed with advantage. The monocarboxylic acid is preferably acetic acid.

It will be obvious to those skilled in the art that it is possible to use starting materials which supply more than one component of the catalyst for example cobalt iodide is a source of both cobalt and iodide. Use of such materials fall within this invention providing to atomic ratio of total iodide or bromide to cobalt is from 0.1:1 to 5:1.

The elevated temperature employed may suitably be in the range from 50° to 350° C., preferably from 80° to 200° C. and pressures can be from 400 to 2500 psig preferably between 900 and 1700 psig. Hydrogen can be present in an amount such that the ratio of the partial pressure of carbon monoxide to hydrogen is at least 5:1 preferably at least 10:1. High ratios of $CO:H_2$ favour acetic anhydride formation over ethylidene diacetate, lower ratios favour formation of ethylidene diacetate. It is preferable, therefore, that if possible hydrogen is absent or substantially absent, although small amounts of hydrogen, as found in commercial carbon monoxide sources, can be tolerated.

The process may be carried out in the liquid phase or in the vapour phase. In the case of both liquid and vapour phase operation, the catalyst and optionally also the promoter combination may be supported, ie they may be dispersed on a conventional support material, such as for example alumina, silica, silica/alumina, zeolites, clays, titania or zirconia. The catalyst and optionally the promoter may be applied to the support in conventional manner, eg by impregnation from solution. The catalyst concentration on the support may suitably be in the range from 0.01 to 10% by weight.

The process of the invention may be carried out batchwise or continuously.

The invention is illustrated by the following examples.

In all the following Examples all the reactants and products except the CO and hydrogen were supplied in the liquid phase and the catalyst and promoter were employed in solution.

EXAMPLE 1

Preparation of acetic anhydride and EDA: hydrogen present

Methyl acetate (35 g), acetic acid (15 g), methyl p-toluenesulphonate (10 g), $Co_2(CO)_8$ (0.2 g), N-methylimidazole (2.3 g) and sodium iodide (0.5 g), iodide:cobalt atomic ratio 3:1 were charged to a stainless steel autoclave which was pressured to 100 psig $H_2$ and to a further 1020 psig with CO at room temperature. This vessel was then heated and stirred for one hour at 130° C. At this temperature the initial total pressure was approximately 1300 psig.

Gas Chromatographic (G.C.) analysis of the reaction mixture showed it to contain 0.6 g of acetic anhydride and 1.0 g of ethylidene diacetate.

EXAMPLE 2

Preparation of acetic anhydride: hydrogen absent

Dimethyl ether (2.1 g), acetic acid (40 g), $Co_2(CO)_8$ (0.4 g), methyl p-toluenesulphonate (12 g), N-methylimidazole (4 g) and sodium iodide (0.5 g), iodide:cobalt atomic ratio 1.5:1, were charged to a stainless steel autoclave which was pressured to 1200 psig with CO at room temperature. The vessel was then heated and stirred for one hour at 150° C. At this temperature the initial pressure was 1400 psig.

Analysis of the reaction product mixture by gas chromatography (G.C.) showed it to contain 1.5 g of methyl acetate and 1.7 g of the acetic anhydride.

EXAMPLE 3

Preparation of acetic anhydride: hydrogen absent

A stainless steel autoclave was charged with a mixture of methyl acetate (35 g), acetic acid (15 g), $Co_2(CO)_8$ (0.4 g), methyl p-toluenesulphonate (12 g), N-methylimidazole (5.3 g) and sodium iodide (0.5 g), iodide:cobalt atomic ratio 1.5:1.

CO (1100 psig) was then added to the autoclave at room temperature. The vessel was heated and stirred for one hour at 150° C. At this temperature the initial pressure in the reactor was 1300 psig.

G.C. analysis of the reaction product mixture showed it to contain 2.7 g of acetic anhydride at the end of the 1 hour reaction.

One advantage of the above described catalyst systems is that they are low in iodide and therefore less corrosive than those described in the prior art.

I claim:

1. A process for the preparation of acetic anhydride by reacting at elevated temperature methyl acetate or dimethyl ether with carbon monoxide characterised in that the reaction is carried out in the presence of an effective amount of a catalyst comprising:
   (1) cobalt,
   (2) a compound containing at least one quaternary nitrogen or phosphorus atom, wherein said compound containing at least one quaternary nitrogen or phosphorus atom is added as two precursors, the first being a trivalent nitrogen or phosphorus compound capable of forming the quaternary compound under the reaction conditions, the second being a halide-free quaternising agent, and
   (3) a source of iodide or bromide wherein the atomic ratio of iodide or bromide to cobalt is from 0.5:1 to 5:1.

2. A process as claimed in claim 1 characterised in that the halide-free quaternizing agent is an alkylating agent.

3. A process as claimed in claim 2, characterised in that the alkylating agent is a methylating agent.

4. A process as claimed in claim 2 characterised in that the alkylating agent is a sulphonate or sulphate ester.

5. A process as claimed in claim 4 characterised in that the alkylating agent is methyl p-toluenesulphonate.

6. A process as claimed in claim 1 characterised in that a lower monocarboxylic acid is added.

7. A process as claimed in claim 6, characterised in that the lower monocarboxylic acid added is acetic acid.

8. A process as claimed in claim 1 characterised in that the temperature is in the range 50° to 350° C. and the pressure in the range 400 to 2500 psig.

9. A process as claimed in claim 8 characterised in that the temperature is in the range 80° to 200° C. and the pressure in the range 900 to 1700 psig.

10. A process as claimed in claim 1 characterised in that hydrogen, if present, is in an amount such that its partial pressure is not more than 10% of the total pressure of carbon monoxide and hydrogen.

* * * * *